United States Patent
Sekiguchi et al.

(10) Patent No.: US 7,713,191 B2
(45) Date of Patent: May 11, 2010

(54) BALLOON CONTROLLER FOR ENDOSCOPE APPARATUS

(75) Inventors: Tadashi Sekiguchi, Saitama (JP); Tetsuya Fujikura, Saitama (JP)

(73) Assignee: Fujinon Corporation, Saitama (JP)

( * ) Notice: Subject to any disclaimer, the term of this patent is extended or adjusted under 35 U.S.C. 154(b) by 945 days.

(21) Appl. No.: 11/265,086

(22) Filed: Nov. 3, 2005

(65) Prior Publication Data

US 2006/0116549 A1    Jun. 1, 2006

(30) Foreign Application Priority Data

Nov. 4, 2004    (JP)    ............................. 2004-321219

(51) Int. Cl.
   *A61B 1/015*    (2006.01)
   *A61M 29/02*    (2006.01)

(52) U.S. Cl. ................. 600/116; 600/115; 600/117; 600/118; 604/97.03; 604/100.01

(58) Field of Classification Search ................. 600/115, 600/116, 103, 114, 117, 118; 604/97.03, 604/96.01, 100.01
   See application file for complete search history.

(56) References Cited

U.S. PATENT DOCUMENTS

| | | | | |
|---|---|---|---|---|
| 4,310,878 A * | 1/1982 | Hyatt | ........................... | 700/78 |
| 4,377,836 A * | 3/1983 | Elms et al. | .................... | 361/96 |
| 4,693,704 A * | 9/1987 | Ogita | ......................... | 604/515 |
| 5,090,259 A * | 2/1992 | Shishido et al. | ............ | 73/866.5 |
| 5,201,753 A | 4/1993 | Lampropoulous et al. | | |
| 5,273,537 A | 12/1993 | Haskvitz et al. | | |
| 5,599,301 A * | 2/1997 | Jacobs et al. | .................. | 604/65 |
| 5,749,853 A * | 5/1998 | O'Donnell et al. | ....... | 604/97.03 |
| 6,394,977 B1 * | 5/2002 | Taylor et al. | ........... | 604/100.03 |
| 2002/0045854 A1* | 4/2002 | Royo et al. | .............. | 604/97.03 |
| 2003/0065250 A1* | 4/2003 | Chiel et al. | .................. | 600/115 |
| 2004/0230157 A1* | 11/2004 | Perry et al. | .............. | 604/99.02 |
| 2005/0159702 A1* | 7/2005 | Sekiguchi et al. | ......... | 604/99.01 |
| 2005/0234293 A1* | 10/2005 | Yamamoto et al. | .......... | 600/102 |

FOREIGN PATENT DOCUMENTS

| | | |
|---|---|---|
| EP | 1 582 141 A1 | 10/2005 |
| JP | 58-138430 A | 8/1983 |
| JP | 1-297036 A | 11/1989 |
| JP | 2002-301019 A | 10/2002 |
| JP | 2003-144378 A | 5/2003 |
| WO | WO-02/064195 A2 | 8/2002 |

* cited by examiner

*Primary Examiner*—John P Leubecker
(74) *Attorney, Agent, or Firm*—Birch, Stewart, Kolasch & Birch, LLP

(57) ABSTRACT

A balloon controller for an endoscope apparatus which enables an operator to correctly and immediately grasp circumstances relating to an abnormal condition at the time of occurrence of the abnormal condition. The balloon controller controls expansion and shrinkage of each of a first balloon attached to an insertion portion of an endoscope and a second balloon attached to an insertion assist implement, by supplying air to the balloon or drawing air from the balloon. Pressure indicating portions on which the values of pressures in the first and second balloons are displayed are provided in a front surface of a main body of the balloon controller. When an abnormal condition occurs, an error code and the pressure values are alternately displayed on the pressure indicating portions.

10 Claims, 13 Drawing Sheets

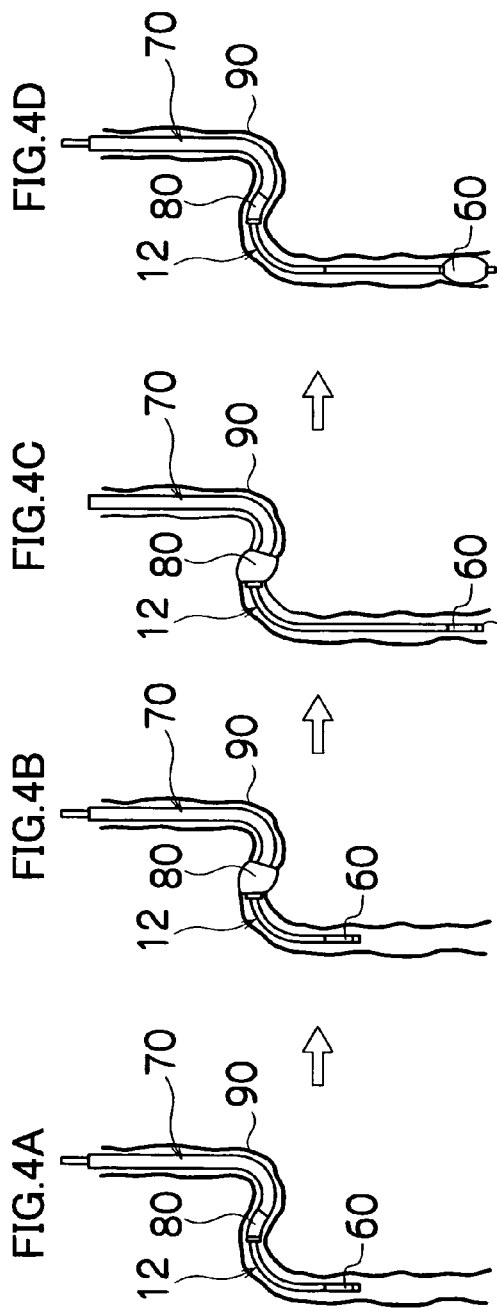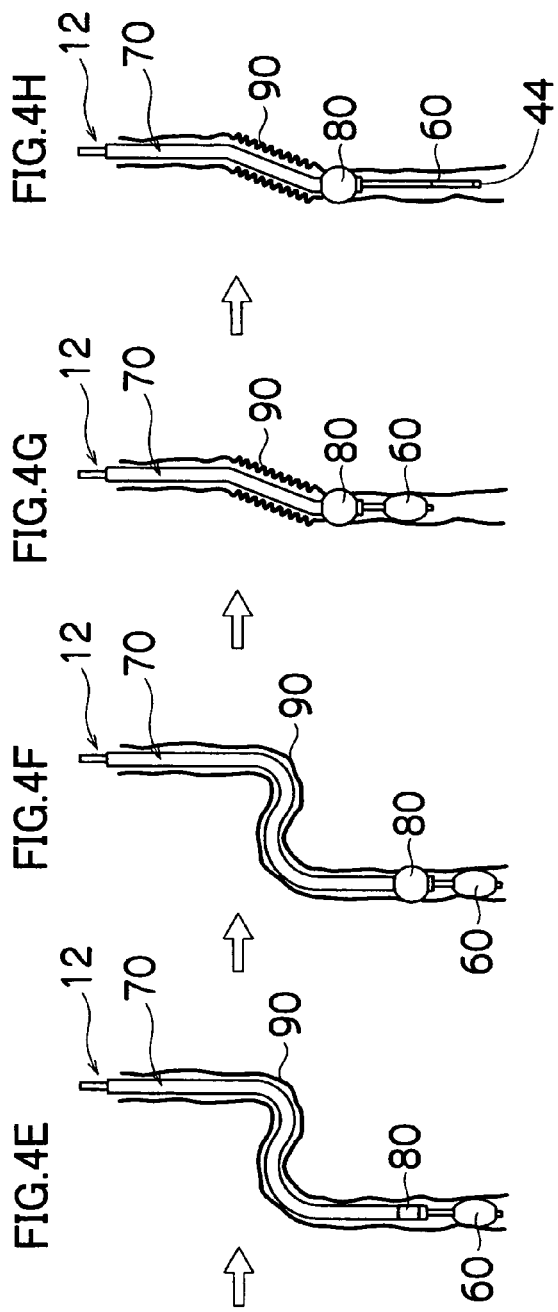

BALLOON CONTROLLER FOR ENDOSCOPE APPARATUS

BACKGROUND OF THE INVENTION

1. Field of the Invention

The present invention relates to a balloon controller for an endoscope apparatus and, more particularly, to a balloon controller for controlling a balloon used in an endoscope apparatus for observing a deep-part digestive tract such as the small intestine or the large intestine.

2. Description of the Related Art

When an insertion portion of an endoscope is inserted into a deep-part digestive tract such as the small intestine, a force for insertion cannot be easily transmitted to the foremost end of the insertion portion due to the existence of complicated bends in the intestinal tract and it is difficult to insert the insertion portion to a deep part, if the insertion portion is simply forced into the tract. For example, if an unnecessary bend or warp is caused in the insertion portion, the insertion portion cannot be inserted to a deeper portion of the tract. A method has therefore been proposed in which the insertion portion of an endoscope is inserted into a body cavity together with an insertion assist implement which covers the insertion portion, and an unnecessary bend or warp in the insertion portion is prevented by guiding the insertion portion with the insertion assist implement.

Japanese Patent Application Laid-Open No. 2002-301019 discloses an endoscope apparatus in which a first balloon is provided on an insertion portion of an endoscope close to the foremost end of the insertion portion and a second balloon is provided on an insertion assist implement (also referred to as an over tube or sliding tube) close to the foremost end of the insertion assist implement. The first and second balloons can fix the insertion portion and the insertion assist implement in the intestinal tract such as the small intestine by expanding the first and second balloons. This endoscope apparatus is capable of inserting the insertion portion to a deep portion of an intestinal tract such as the small intestine having complicated bends by alternately inserting the insertion portion and the insertion assist implement while repeating expanding and shrinking the first and second balloons.

Japanese Patent Application Laid-Open No. 2003-144378 discloses a balloon controller which controls supply of air to a balloon and drawing of air from the balloon. In a front face of a main unit of this balloon controller are provided a plurality of display panels, on which a set pressure and time for reaching to the set pressure at the time of supply or drawing of air are indicated, and a plurality of warning lamps, each of which is lighted when the pressure or time exceeds a threshold value. When an abnormality occurs, the corresponding warning lamp is lighted to enable an operator to recognize the abnormality.

SUMMARY OF THE INVENTION

However, the balloon controller disclosed in Japanese Patent Application Laid-Open No. 2003-144378 is provided with a number of display panels and a number of warning lamps and, therefore has a problem that the manufacturing cost and the size of the controller are increased. This balloon controller also has a problem that an operator is liable to be unaware of lighting of a warning lamp in ordinary cases of operating while viewing an observed image obtained through an endoscope and reading an indication on a pressure gauge for the balloon and cannot immediately grasp what kind of error has occurred and the value of pressure in the balloon in the abnormal condition even if he or she notices lighting of a warning lamp.

In view of these circumstances, an object of the present invention is to provide a balloon controller for an endoscope which enables an operator to correctly and immediately grasp circumstances relating to an abnormal condition at the time of occurrence of the abnormal condition.

To achieve the above-described object, according to a first aspect of the present invention, there is provided a balloon controller for an endoscope apparatus which is connected to a balloon attached to an insertion portion of an endoscope or to a balloon attached to an insertion assist implement for guiding the insertion portion when the insertion portion is inserted, and which controls expansion and shrinkage of the balloon by supplying a fluid to the balloon or drawing the fluid from the balloon, the balloon controller comprising a pressure indicating portion on which the value of pressure in the balloon is displayed, wherein an error message indicating an abnormal condition in the endoscope apparatus is displayed on the pressure indicating portion.

According to the first aspect of the present invention, an error message is displayed on the balloon pressure indicating portion. Therefore, an error message can be immediately recognized when an abnormal condition occurs. Also, according to the first aspect of the present invention, there is no need to specially provide a panel and a warning lamp for an error message. As a result, the cost and size of the controller can be reduced.

According to a second aspect of the present invention, there is provided a balloon controller for an endoscope apparatus which is connected to a balloon attached to an insertion portion of an endoscope and to a balloon attached to an insertion assist implement for guiding the insertion portion when the insertion portion is inserted, and which controls expansion and shrinkage of each balloon by supplying a fluid to the balloon or drawing the fluid from the balloon, the balloon controller comprising: a pressure indicating portion on which the value of pressure in the balloon on the endoscope side is displayed, and an another pressure indicating portion on which the value of pressure in the balloon on the insertion assist implement side is displayed, wherein when an abnormal condition of one of the two balloons occurs, an error message is displayed on the pressure indicating portion corresponding to the balloon having the abnormal condition.

According to the second aspect of the present invention, an error message is displayed on the balloon pressure indicating portions. Therefore, the occurrence of an abnormal condition can be immediately grasped and the cost and size of the controller can be reduced.

Also, according to the second aspect of the present invention, an error message is displayed on one of the pressure indicating portions when an abnormal condition of the corresponding balloon occurs. Therefore, one of the balloons having an abnormal condition can be immediately recognized.

According to a third aspect of the present invention, the error message and the value of pressure in the balloon are alternately displayed on the pressure indicating portion in the balloon controller according to the first or second aspect of the invention.

According to the third aspect of the present invention, the error message and the value of pressure in the balloon are alternately displayed on the pressure indicating portion. Therefore, even when the apparatus is in an abnormal condition, the value of pressure in the balloon can be recognized and the state of expansion/shrinkage of the balloon can be grasped. Consequently, circumstances under which the abnormal condition has occurred can be accurately grasped.

According to a fourth aspect of the present invention, the error message is displayed as an error code having a numeric figure indicating the kind of the abnormal condition in the balloon controller according to any of the first to third aspects of the invention.

According to the fourth aspect of the present invention, the error message is displayed as an error code, i.e., a numeric figure and, therefore, a panel of a simple structure on which a numeric figure is displayed may be used. As a result, the size and cost of the controller can be reduced.

According to a fifth aspect of the present invention, the pressure indicating portion is provided on a main body of the balloon controller according to any one of the first to fourth aspects of the invention.

In the balloon controller for an endoscope apparatus in accordance with the present invention, an error message is displayed on a balloon pressure indicating portion. This arrangement ensures that the occurrence of an abnormal condition can be immediately and accurately grasped, and that the size and cost of the controller can be reduced.

BRIEF DESCRIPTION OF THE DRAWINGS

FIGS. 4A to 4H are diagrams showing the method of operating the endoscope apparatus in accordance with the present invention;

DETAILED DESCRIPTION OF THE PREFERRED EMBODIMENTS

Figure 1:
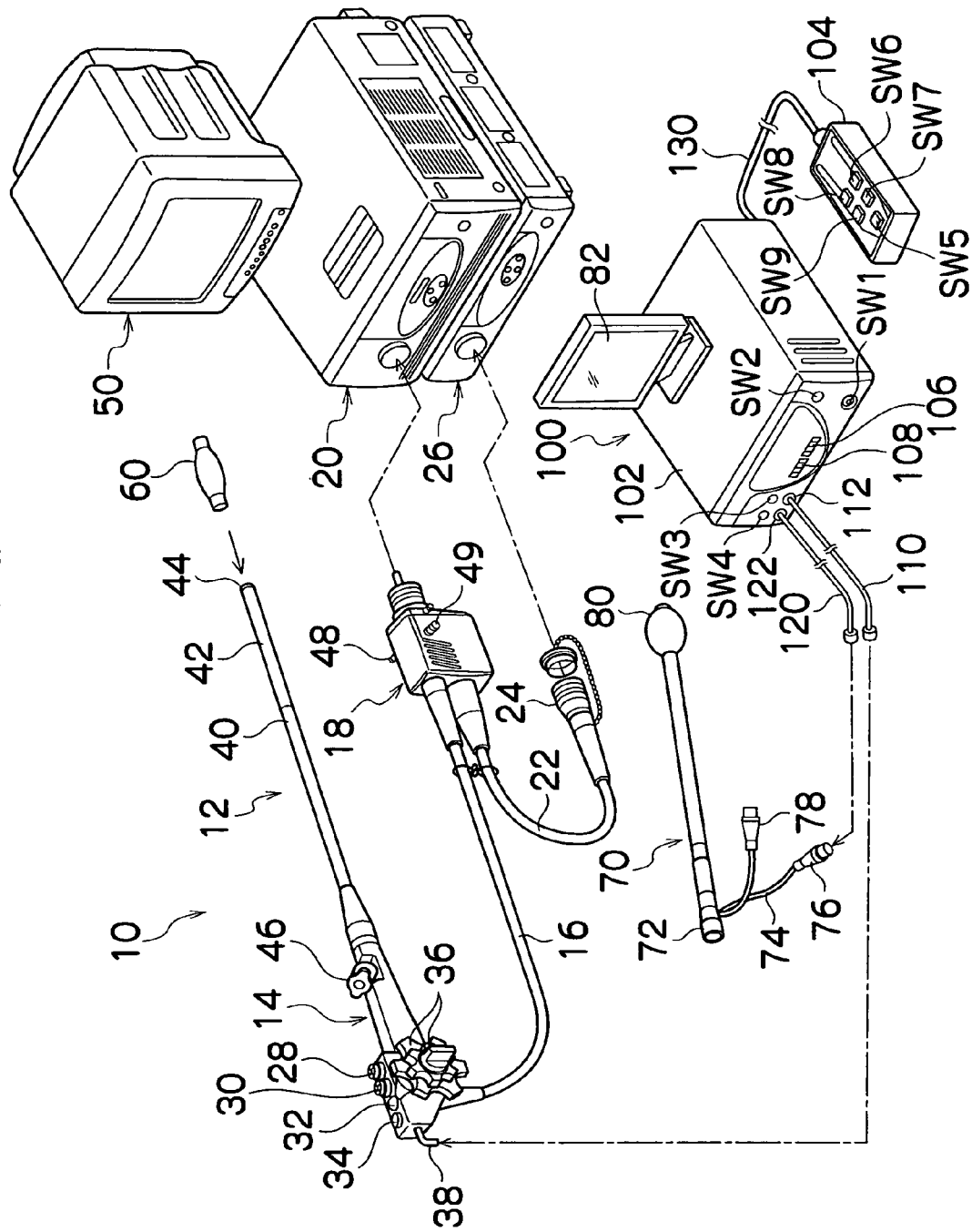
FIG. 1 is a diagram showing a system configuration of an endoscope apparatus in accordance with the present invention.

A preferred embodiment of a balloon controller for an endoscope apparatus in accordance with the present invention will be described with reference to the accompanying drawings. FIG. 1 is a diagram showing a system configuration representing an implementation of an endoscope apparatus to which a balloon controller in accordance with the present invention is applied. As shown in FIG. 1, the endoscope apparatus is constituted mainly by an endoscope 10, an insertion assist implement 70 and a balloon controller 100.

As shown in FIG. 1, the endoscope 10 has an at-hand operating portion 14 and an insertion portion 12 which is joined to the at-hand operating portion 14, and which is inserted into a body cavity. One end of a universal cable 16 is connected to the at-hand operating portion 14, and an LG connector 18 is provided at the other end of the universal cable 16. The LG connector 18 is detachably attached to a light source unit 20 to enable transmission of illumination light to an illumination optical system 54 (see FIG. 2) described below. An electric connector 24 is connected to the LG connector 18 via a cable 22 and is detachably attached to a processor 26.

On the at-hand operating portion 14, an air/water supply button 28, an aspiration button 30, a shutter button 32 and a function change button 34 are provided one adjacent to another and a pair of angle knobs 36 are provided. A balloon air supply port 38 is formed at a base end of the at-hand operating portion 14 by a tube bent into L shape. A fluid such as air is supplied to or drawn from the balloon air supply port 38 to expand or shrink a first balloon 60 described below.

The insertion portion 12 includes a soft portion 40, a bending portion 42 and a foremost end portion 44 provided in this order from the at-hand operating portion 14 side. The bending portion 42 is remotely operated by rotating the angle knobs 36 on the at-hand operating portion 14 so that the bending portion 42 bends. In this way, the foremost end portion 44 can be directed as desired.

Figure 2:
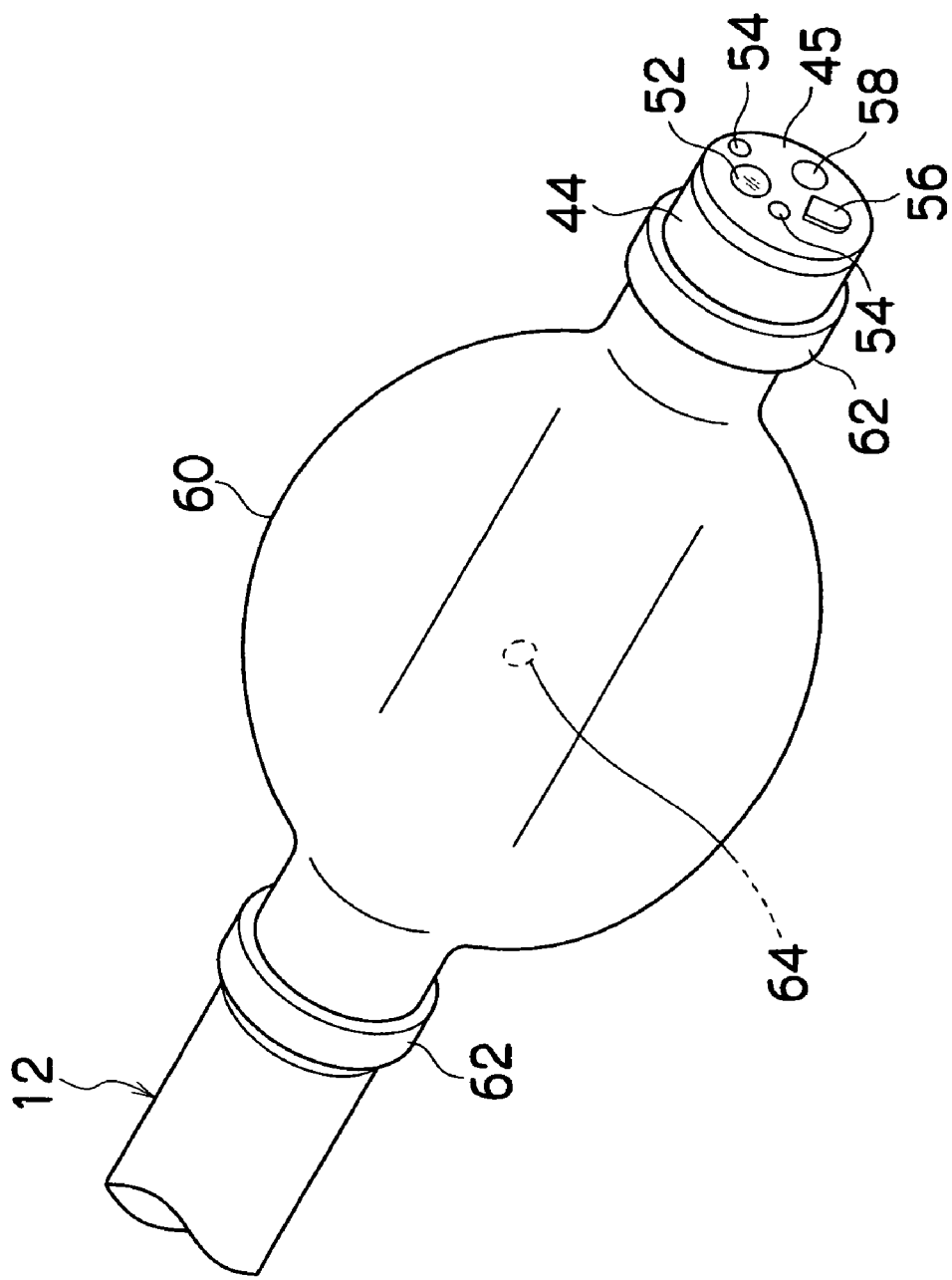
FIG. 2 is a perspective view of a fore end of an insertion portion of an endoscope.

As shown in FIG. 2, an observation optical system 52, illumination optical systems 54, an air/water supply nozzle 56 and a forceps opening 58 are provided in a foremost end surface 45 of the foremost end portion 44. A charge-coupled device (CCD) (not shown) is provided at the rear of the observation optical system 52, and a signal cable (not shown) is connected to a base plate on which the CCD is supported. The signal cable is extended to the electric connector 24 by being passed through the insertion portion 12, the at-hand operating portion 14, the universal cable 16 and other components shown in FIG. 1 to be connected to the processor 26. An observed image taken through the observation optical system 52 is imaged on the light receiving surface of the CCD to be converted into an electrical signal. This electrical signal is output to the processor 26 via the signal cable to be converted into a video signal, thus enabling the observed image to be displayed on a monitor 50 connected to the processor 26.

At the rear of the illumination optical systems 54 shown in FIG. 2, an emergence end of a light guide (not shown) is provided. This light guide is passed through the insertion portion 12, the at-hand operating portion 14 and the universal cable 16 shown in FIG. 1 and has its incidence end placed in the LG connector 18. The LG connector 18 is connected to a light source unit 20 to enable illumination light emitted from the light source unit 20 to be transmitted to the illumination optical systems 54 through the light guide and radiated forward from the illumination optical systems 54.

The air/water supply nozzle 56 shown in FIG. 2 communicates with a valve (not shown) operated with the air/water supply button 28 shown in FIG. 1. This valve communicates with an air/water supply connector 48 provided in the LG connector 18. An air/water supply device (not shown) is connected to the air/water supply connector 48 to supply air or water. Air or water can be jetted from the air/water supply nozzle 56 toward the observation optical system 52 by operating the air/water supply button 28.

The forceps opening 58 shown in FIG. 2 communicates with a forceps insertion portion 46 shown in FIG. 1. An implement for a treatment such as forceps can be inserted through the forceps insertion portion 46 and guided to the forceps opening 58 to project from the same. The forceps opening 58 also communicates with a valve (not shown) operated with the aspiration button 30. This valve is connected to an aspiration connector 49 in the LG connector 18. An aspiration device (not shown) can be connected to the aspiration connector 49 to suck a lesion portion or the like through the forceps opening 58 by operating the valve by means of the aspiration button 30.

The first balloon 60 made of an elastic material such as rubber is fitted around the outer peripheral surface of the insertion portion 12. The first balloon 60 is formed into a generally cylindrical shape constricted at its opposite ends. The insertion portion 12 is passed through the first balloon 60 and the first balloon 60 is placed in a desired position on the insertion portion 12. Thereafter, fixing rings 62 made of rubber are fitted around opposite end portions of the first balloon 60, as shown in FIG. 2, thus fixing the first balloon 60 on the insertion portion 12.

An air hole 64 is formed in the outer peripheral surface of the insertion portion 12 at a position corresponding to the attached position of the first balloon 60. The air hole 64 communicates with the balloon air supply port 38 provided in the at-hand operating portion 14 shown in FIG. 1. The balloon air supply port 38 is connected to the balloon controller 100 via a tube 110 described below. The first balloon 60 can be expanded or shrunk by the balloon controller 100 supplying or drawing air. When air is supplied to the first balloon 60, the first balloon 60 expands so as to be generally spherical. When air is drawn, the first balloon 60 adheres to the outer surface of the insertion portion 12.

The insertion assist implement 70 shown in FIG. 1 is formed into a cylindrical shape, has an inside diameter slightly larger than the outside diameter of the insertion portion 12, and has sufficiently high flexibility. The insertion assist implement 70 has a hard hold portion 72 at its base end. The insertion portion 12 is inserted into the insertion assist implement 70 through the hold portion 72.

A second balloon 80 is attached to the insertion assist implement 70 in the vicinity of the foremost end of the insertion assist implement 70. The second balloon 80 is formed into a generally cylindrical shape constricted at its opposite ends. The second balloon 80 is attached to the insertion assist implement 70 passed through the second balloon 80 and is fixed on the insertion assist implement 70 by winding a string (not shown). A tube 74 attached to the outer peripheral surface of the insertion assist implement 70 communicates with the second balloon 80. A connector 76 is provided on an end portion of the tube 74, and a tube 120 is connected to the connector 76. The tube 120 is connected to the balloon controller 100. The balloon controller 100 supplies or draws air through the tube 120 to expand or shrink the second balloon 80. When air is supplied to the second balloon 80, the second balloon 80 expends so as to be generally spherical. When air is drawn from the second balloon 80, the second balloon 80 adheres to the outer peripheral surface of the insertion assist implement 70.

An injection port 78 is provided at the base end of the insertion assist implement 70. The injection port 78 communicates with an opening (not shown) formed in an inner peripheral surface of the insertion assist implement 70. A lubricant (e.g., water) can be supplied to the interior of the insertion assist implement 70 by being injected from an injector or the like through the injection port 78. The lubricant can reduce friction between the inner peripheral surface of the insertion assist implement 70 and the outer peripheral surface of the insertion portion 12 when the insertion portion 12 is inserted in the insertion assist implement 70 to enable the insertion portion 12 and the insertion assist implement 70 to smoothly move relative to each other.

The balloon controller 100 supplies a fluid such as air to the first balloon 60 or draws the fluid from the first balloon 60 and also supplies a fluid such as air to the second balloon 80 or draws the fluid from the first balloon 80. The balloon controller 100 is constituted mainly by a main unit 102 and a hand switch 104 for remote control.

Figure 3:
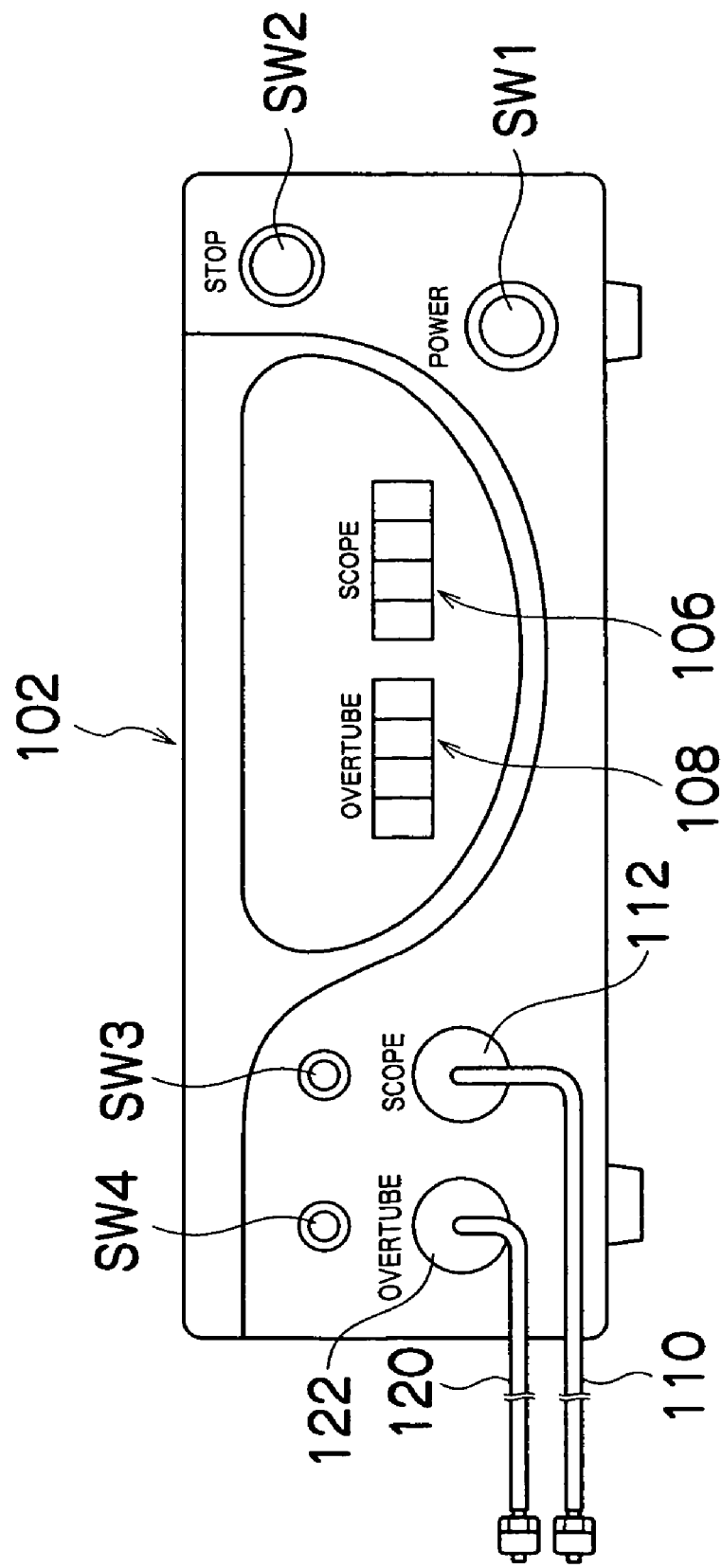
FIG. 3 is a front view of a front panel of a balloon controller.

As shown in FIG. 3, a power supply switch SW1, a stop switch SW2, a first pressure indicating portion 106, a second pressure indicating portion 108, a first function stop switch SW3 and a second function stop switch SW4 are provided in a front surface of the main unit 102. The first pressure indicating portion 106 and the second pressure indicating portion 108 are panels on which the values of pressures in the first balloon 60 and the second balloon 80 are respectively indicated. An error code is displayed on the pressure indicating portion 106 or 108 when an abnormality such as a break in the corresponding balloon occurs.

The first function stop switch SW3 and the second function stop switch SW4 are switches by which an endoscope control system A and an insertion assist implement control system B described below are respectively turned on or off to function or stop functioning. When only one of the first balloon 60 and the second balloon 80 is used, the function stop switch SW3 or SW4 corresponding to the balloon not used is operated to stop functioning. In the control system A or B stopped from functioning, supply or drawing of air is completely stopped and the pressure indicating portion 106 or 108 is also off. Both the function stop switches SW3 and SW4 may be turned off to enable initialization or the like. For example, calibration with respect to ambient pressure is performed by turning off both the function stop switches SW3 and SW4 and by pressing all switches SW5 to SW9 in the hand switch 104.

In the front surface of the main unit 102, the tube 110 for supply of air to the first balloon 60 and for drawing of air from the first balloon 60 and the tube 120 for supply of air to the second balloon 80 and for drawing of air from the second balloon 80 are connected. The tubes 110 and 120 are connected to the main unit 102 through connection portions including back-flow preventing units 112 and 122 each for preventing a backward flow of a body fluid when the first or second balloon 60 or 80 is broken. Each of the back-flow preventing units 112 and 122 is constructed by incorporating a gas/liquid disengagement filter in a case in the form of a hollow disk detachably attached to the main unit 102 to prevent the fluid from flowing into the main unit 102 by the filter.

The pressure indicating portions 106 and 108, the function stop switches SW3 and SW4 and back-flow preventing units 112 and 122 are disposed in a fixed configuration by being divided into a group for the endoscope 10 and a group for the insertion assist implement 70. That is, the pressure indicating portion 106, the function stop switch SW3 and the back-flow preventing unit 112 for the endoscope 10 are disposed on the right-hand side of the pressure indicating portion 108, the function stop switch SW4 and the back-flow preventing unit 122 for the insertion assist implement 70.

The switch SW5 provided in the hand switch 104 shown in FIG. 1 is a stop switch similar to the stop switch SW2 on the main unit 102 side. The switch SW6 in the hand switch 104 is an on/off switch by which a command to pressurize or depressurize the first balloon 60 is input. The switch SW7 in the hand switch 104 is a pause switch for maintaining the pressure in the first balloon 60. The switch SW8 in the hand switch 104 is an on/off switch by which a command to pressurize or depressurize the second balloon 80 is input. The switch SW9 in the hand switch 104 is a pause switch for maintaining the pressure in the second balloon 80. The hand switch 104 is electrically connected to the main unit 102 via a cable 130. The hand switch 104 has a display portion (not shown in FIG. 1) on which the conditions of supply air to the first and second balloons 60 and 80 or the conditions of exhaust of air from the first and second balloons 60 and 80 are displayed.

The balloon controller 100 arranged as described above expands each of the balloons 60 and 80 by supplying air to the balloon 60 or 80, and maintains the balloon 60 or 80 in the expanded state by controlling the air pressure in the balloon at a certain value. Also, the balloon controller 100 shrinks the balloons 60 or 80 by drawing air therefrom, and maintains the balloons 60 or 80 in the shrunken state by controlling the air pressure in the balloon at a certain value.

The balloon controller 100 is connected to a balloon monitor 82 provided specially for monitoring of the balloons 60 and 80. The states of expansion/shrinkage of the balloons 60 and 80 are displayed on the balloon monitor 82. The values of pressures in the balloons 60 and 80 and the states of expansion/shrinkage of the balloons 60 and 80 may be displayed on the monitor 50 by being superimposed on an observed image obtained by the endoscope 10.

The method of operating the endoscope apparatus constructed as described above will be described with reference to FIGS. 4A to 4H.

Referring to FIG. 4A, the insertion portion 12 is first inserted into an intestinal tract (e.g., a descending part of the duodenum) 90, with the insertion assist implement 70 fitted around the insertion portion 12. At this time, the first and second balloons 60 and 80 are maintained in the shrunken state.

Air is thereafter supplied to the second balloon 80 to expand the second balloon 80 in a state where the foremost end of the insertion assist implement 70 is inserted to a bend in the intestinal tract 90, as shown in FIG. 4B. That is, the switch SW8 in the hand switch 104 is turned on to input a pressurization command, thereby supplying air from the balloon controller 100 to the second balloon 80 via the tube 120 so that second balloon 80 expands until an increased pressure set in advance is applied. The second balloon 80 is thereby caught in the intestinal tract 90 to fix the foremost end of the insertion assist implement 70 in the intestinal tract 90.

Subsequently, only the insertion portion 12 of the endoscope 10 is inserted to a deeper portion of the intestinal tract 90, as shown in FIG. 4C. Air is then supplied to the first balloon 60 to expand the first balloon 60, as shown in FIG. 4D. That is, the switch SW6 in the hand switch 104 is turned on to input a pressurization command, thereby supplying air from the balloon controller 100 to the first balloon 60 via the tube 110 so that first balloon 60 expands until an increased pressure set in advance is reached. The first balloon 60 is thereby fixed in the intestinal tract 90.

Subsequently, air is drawn from the second balloon 80 to shrink the second balloon 80. That is, the switch SW8 in the hand switch 104 is turned off to input a depressurization command, thereby drawing air from the second balloon 80 into the balloon controller 100 via the tube 120 so that the second balloon 80 shrinks until a reduced pressure set in advance is reached. Thereafter, the insertion assist implement 70 is forced in to be inserted along the insertion portion 12, as shown in FIG. 4E. After the foremost end of the insertion assist implement 70 has been brought close to the first balloon 60, air is supplied to the second balloon 80 to expand the second balloon 80, as shown in FIG. 4F. That is, the switch SW8 in the hand switch 104 is turned on to expand the second balloon 80 until the increased pressure set in advance is reached. The second balloon 80 is thereby fixed in the intestinal tract 90. That is, the intestinal tract 90 is caught by the second balloon 80.

Subsequently, the insertion assist implement 70 is drawn in, as shown in FIG. 4G. As a result, the intestinal tract 90 contracts and an unnecessary bend or warp in the insertion assist implement 70 is removed. Air is thereafter drawn from the first balloon 60 to shrink the first balloon 60, as shown in FIG. 4H. That is, the switch SW6 in the hand switch 104 is turned off to input a depressurization command, thereby drawing air from the first balloon 60 into the balloon controller 100 via the tube 110 so that the first balloon 60 shrinks until a reduced pressure set in advance is reached.

The amount of insertion of the foremost end 44 of the insertion portion 12 in the intestinal tract 90 is increased as much as possible. That is, an insertion operation such as shown in FIG. 4C is again performed. The foremost end 44 of the insertion portion 12 is thereby inserted to a deeper portion of the intestinal tract 90. To insert the insertion portion 12 to a further deeper portion, a fixing operation such as shown in FIG. 4D, a forcing-in operation such as shown in FIG. 4E, a catching operation such as shown in FIG. 4F, a drawing-in operation such as shown in FIG. 4G and an inserting operation such as shown in FIG. 4H are repeatedly performed one after another. In this way, the insertion portion 12 can be inserted to a further deeper portion of the intestinal tract 90.

Figure 5:
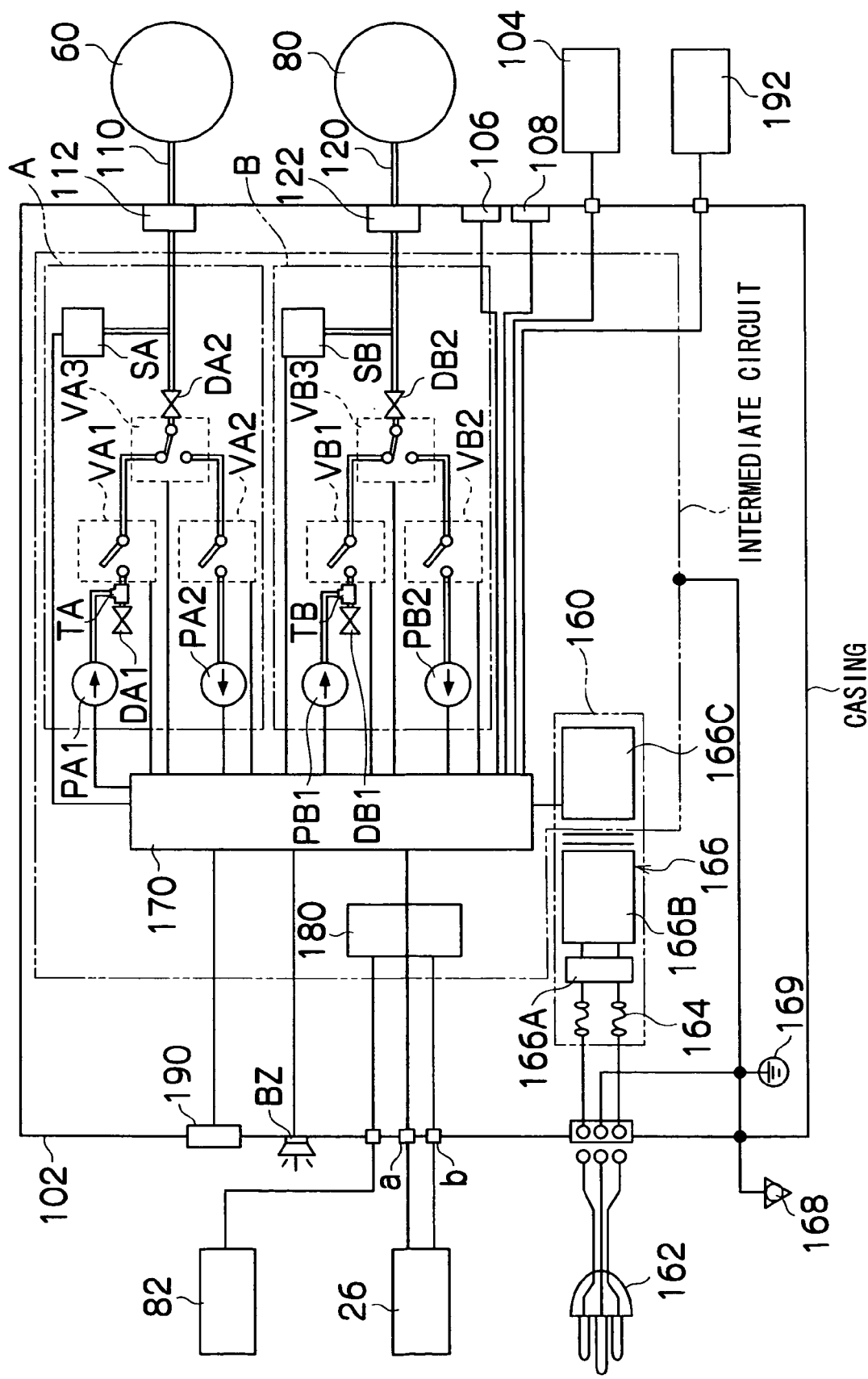
FIG. 5 is a block diagram showing the internal construction of the balloon controller.

The internal construction of the balloon controller 100 will next be described. FIG. 5 is a block diagram showing an example of implementation of the internal construction of the balloon controller 100. As shown in FIG. 5, the main unit 102 of the balloon controller 100 is constituted mainly by a power supply circuit 160, a sequencer 170, the endoscope control system A and the insertion assist implement control system B.

The power supply circuit 160 converts a commercial power input through a power plug 162 into dc power at a required voltage and supplies the dc power to each section in the main unit 102. The power supply circuit 160 is constituted by a fuse 164 and a switching power supply 166. The switching power supply 166 includes a power switch 166A, a primary power section 166B and a secondary power section 166C. Reinforced insulation is provided between the primary power section 166B and the secondary power section 166C. In FIG. 5, reference numeral 168 designates a potential equalization terminal, and reference numeral 169 denotes a protective grounding terminal. An intermediate circuit indicated by the double-dot-dash line is grounded in a protective grounding manner, and a casing indicated by the solid line is also grounded in a protective grounding manner.

The sequencer 170 separately controls the endoscope control system A and the insertion assist implement control system B on the basis of various commands from the hand switch 104 and performs control operations to detect a pressure abnormality or the like, sound a buzzer BZ when detecting an abnormality.

The sequencer 170 is connected to an image processing circuit 180, in which signals representing the values of measurement results obtained by a pressure sensors SA and SB undergo processing for conversion into image signals. The processed signals are sent to the balloon monitor 82 and the states of expansion/shrinkage of the balloons 60 and 80 are graphically displayed on the balloon monitor 82. The image processing circuit 180 is connected to the processor 26. When an observed image signal obtained by the endoscope 10 is input through an input terminal a, a superimposition signal is formed such that the states of expansion/shrinkage of the balloons 60 and 80 are superimposed on the observed image. The superimposition signal is output from an output terminal b to the processor 26, thereby enabling an image in which the states of the balloons are superimposed on the observed image to be displayed on the monitor 50 shown in FIG. 1.

The sequencer 170 is connected to a cooling fan 190 and a foot switch 192. When the power supply switch SW1 (see FIG. 3) is turned on, the cooling fan 190 is driven to blow air into the main unit 102 in order to prevent overheating. The foot switch 192 has a plurality of pedals, which are depressed by an operator to switch between supply of air and exhaust of air or to stop supply or exhaust of air. The operation of the sequencer 170 will be described below in detail.

The endoscope control system A is constituted mainly by a pump PA1 for pressurization, a pump PA2 for depressurization, an electromagnetic valve VA1 for turning on/off supply of air from the pump PA1, an electromagnetic valve VA2 for turning on/off drawing of air with the pump PA2, an electromagnetic valve VA3 for switching between pressurization and depressurization, and the pressure sensor SA for detecting the pressure in the tube 110. Starting/stopping of the pressurizing pump PA1 and the depressurizing pump PA2 is controlled by the sequencer 170. Change of each of the three electromagnetic valves VA1, VA2, and VA3 is controlled by a drive signal from the sequencer 170.

The pressure sensor SA is capable of detecting an increased pressure $P_1$ set in advance (e.g., a pressure higher than ambient pressure by 5.6 kPa), an abnormal pressure $P_2$ higher than the increased pressure $P_1$ (e.g., a pressure higher than ambient pressure by 8.2 kPa) and a reduced pressure $P_3$ set in advance (e.g., a pressure lower than ambient pressure by 6.0 kPa). The pressure detected by the pressure sensor SA is supplied to the sequencer 170 and indicated on the pressure indicating portion 106.

A three-way value VA4 is provided between the pressurizing pump PA1 and the electromagnetic valve VA1, and a fixed aperture DA1 is mounted in the three-way value VA4. Part of air supplied from the pressurizing pump PA1 is released from the fixed aperture DA1 to atmospheric air at all times.

A fixed aperture DA2 is provided between the electromagnetic valve VA3 and the gas/liquid disengagement unit 112. The rate of flow of a fluid in the tube 110 is controlled by the fixed aperture DA2.

The insertion assist implement control system B has the same construction as that of the endoscope control system A. The insertion assist implement control system B is constituted mainly by a pump PB1 for pressurization, a pump PB2 for depressurization, an electromagnetic valve VB1 for turning on/off supply of air from the pump PB1, an electromagnetic valve VB2 for turning on/off drawing of air with the pump PB2, an electromagnetic valve VB3 for switching between pressurization and depressurization, and the pressure sensor SB for detecting the pressure in the tube 120. Starting/stopping of the pressurizing pump PB1 and the depressurizing pump PB2 is controlled by the sequencer 170. Change of each of the three electromagnetic valves VB1, VB2, and VB3 is controlled by a drive signal from the sequencer 170.

The pressure sensor SB is capable of detecting the increased pressure $P_1$ set in advance (e.g., a pressure higher than ambient pressure by 5.6 kPa), the abnormal pressure $P_2$ higher than the increased pressure $P_1$ (e.g., a pressure higher than ambient pressure by 8.2 kPa) and the reduced pressure $P_3$ set in advance (e.g., a pressure lower than ambient pressure by 6.0 kPa). The pressure detected by the pressure sensor SB is supplied to the sequencer 170 and indicated on the pressure indicating portion 108.

A three-way value VB4 is provided between the pressurizing pump PB1 and the electromagnetic valve VB1, and a fixed aperture DB1 is mounted in the three-way value VA4. Part of air supplied from the pressurizing pump PB1 leaks from the fixed aperture DB1 at all times.

A fixed aperture DB2 is provided between the electromagnetic valve VB3 and the gas/liquid disengagement unit 122. The rate of flow of a fluid in the tube 120 is controlled by the fixed aperture DB2.

The operation of the sequencer 170 will be described in detail with reference to the flowcharts of FIGS. 6 to 9. The way in which endoscope balloon control is performed by the sequencer 170 and the way in which insertion assist implement balloon control is performed by the sequencer 170 are the same. Therefore, the description will be made only of the endoscope balloon control.

Figure 6:
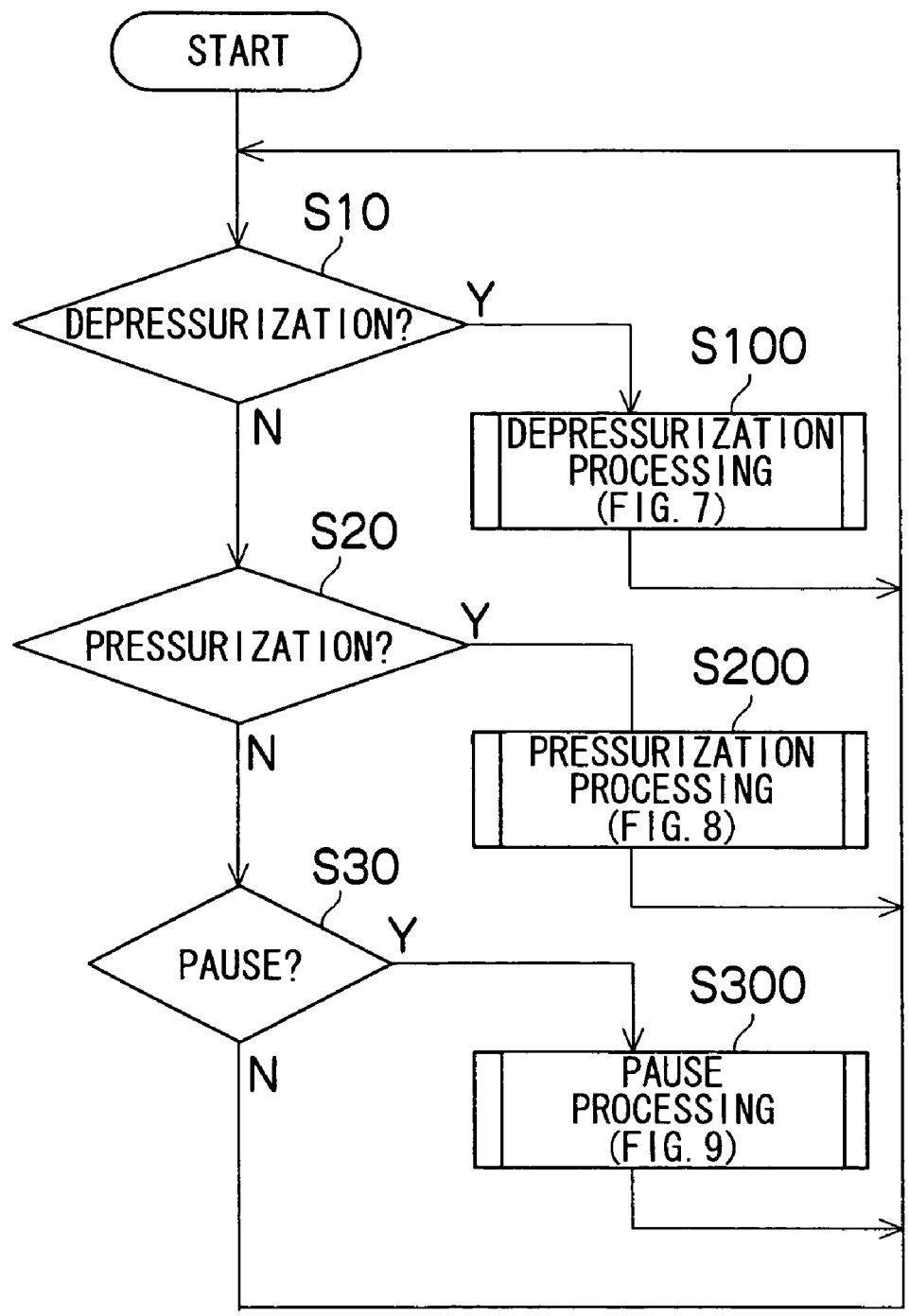
FIG. 6 is a flowchart showing the outline of the operation of a sequencer shown in FIG. 5.

FIG. 6 is a flowchart showing the outline of the operation of the sequencer 170. In this figure, the sequencer 170 determines whether or not a first balloon 60 depressurization command (i.e. a command input by turning off the switch SW6) has been input from the hand switch 104 (step S10). If the depressurization command has been input, the sequencer 170 executes depressurization processing shown in FIG. 7.

Similarly, the sequencer 170 determines whether or not a first balloon 60 pressurization command (i.e. a command input by turning on the switch SW6) has been input from the hand switch 104 and whether or not a pause command to maintain the pressure in the balloon 60 (i.e., a command input by turning on the pause switch SW7) has been input from the hand switch 104 (steps S20 and S30). If the pressurization command has been input, the sequencer 170 executes pressurization processing shown in FIG. 8. If the pause command has been input, the sequencer 170 executes pause processing shown in FIG. 9.

A green light emitting diode (LED) and a white LED are respectively provided in key tops of the switch SW6 and the pause switch SW7. Each of the green LED and the white LED is lighted when the switch is turned on. Also, a green LED and a white LED are respectively provided in the switch SW8 and the pause switch SW9.

Figure 7:
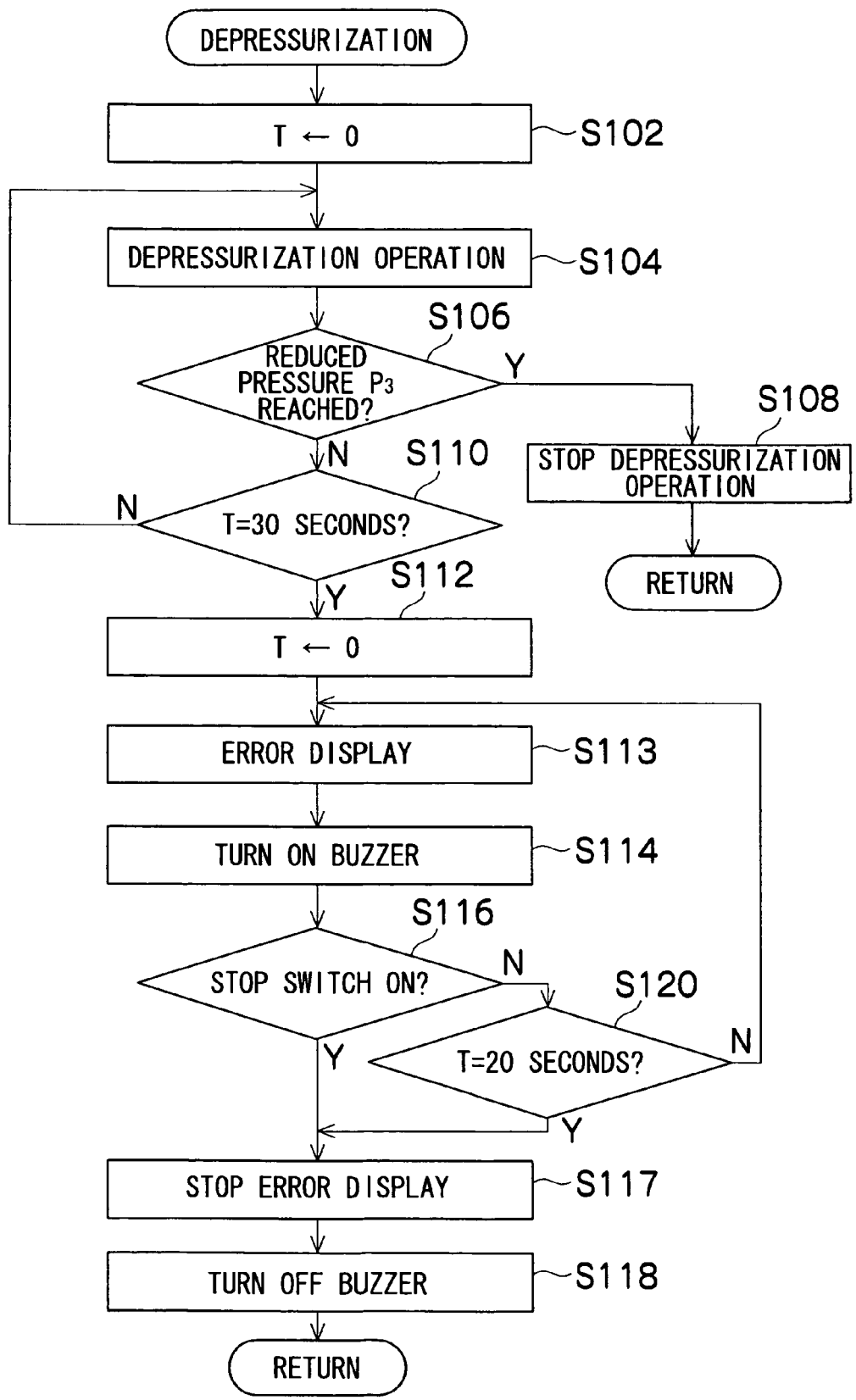
FIG. 7 is a flowchart showing the operation with respect to depressurization processing shown in FIG. 6.

Depressurization processing will be described with reference to the flowchart of FIG. 7.

The sequencer 170 first resets time T in a timer for measuring time to 0 (step S102) and thereafter operates the control system A for depressurization (step S104). That is, the sequencer 170 turns off the electromagnetic valves VA1, VA2, and VA3 shown in FIG. 5, and drives the pump PA2 for depressurization.

Subsequently, the sequencer 170 determines from the detection signal from the pressure sensor SA whether or not the pressure in the tube 110 has reached the reduced pressure $P_3$ set in advance (step S106). If the pressure in the tube 110 has reached the reduced pressure $P_3$, the sequencer 170 stops the depressurization operation (step S108).

The depressurization operation is stopped by means of the electromagnetic valve VA2. Since the diameter of the air supply tube provided along the insertion portion 12 of the balloon-type endoscope 10 is sufficiently smaller than the diameter of the tube 110, the pressure in the tube 110 reaches the reduced pressure $P_3$ before the pressure in the first balloon 60 reaches the reduced pressure $P_3$ after the start of drawing of air (depressurization). The depressurization operation is thereby stopped. However, if the pressure in the first balloon 60 has not reached the reduced pressure $P_3$, the pressure in the tube 110 is again increased to become higher than the reduced pressure $P_3$. In this case, the sequencer 170 again starts the depressurization operation by referring to the detection signal from the pressure sensor SA2. Thus, starting the depressurization operation and stopping the depressurization operation are repeated a certain number of times to adjust the pressure in the first balloon 60 to the reduced pressure $P_3$.

On the other hand, if the reduced pressure $P_3$ has not been reached, the sequencer 170 determines whether or not time T after the start of depressurization operation has reached 30 seconds (step S110). In the case of repeating the processing through step S104, S106, and S110 before time T reaches 30 seconds, the sequencer 170 determines that there is an abnormality (for example, the tube 110 and the balloon air supply port 18 are not connected).

If the sequencer 170 detects an abnormality as described above, it resets time T in the timer to 0, displays an error message and simultaneously sounds the buzzer BZ (steps S112, S113, and S114). As the error message, an error code (e.g., "Err7") and the value of pressure in the first balloon 60 are alternately displayed on the pressure indicating portion 106. The sequencer 170 simultaneously lights red LEDs provided in key tops of the stop switch SW2 provided on the main unit 102 and the stop switch SW3 provided in the hand switch 104.

The sequencer 170 thereafter determines whether the stop switch SW2 or SW5 is pressed (step S116). If the stop switch is pressed, the sequencer 170 stops displaying the error message and sounding the buzzer BZ (steps S117 and S118). If neither of the stop switch SW2 nor SW5 is pressed, the sequencer 170 determines whether or not a time period of 20 seconds has lapsed. If a time period of 20 seconds has lapsed, the sequencer 170 automatically stops sounding the buzzer BZ.

When the operator of the double-balloon-type endoscope is notified of an abnormality during the above-described depressurization operation by means of the buzzer BZ for example, he or she presses the stop switch SW2 or SW5 and checks, for example, whether or not the tube 110 is connected.

Figure 8:
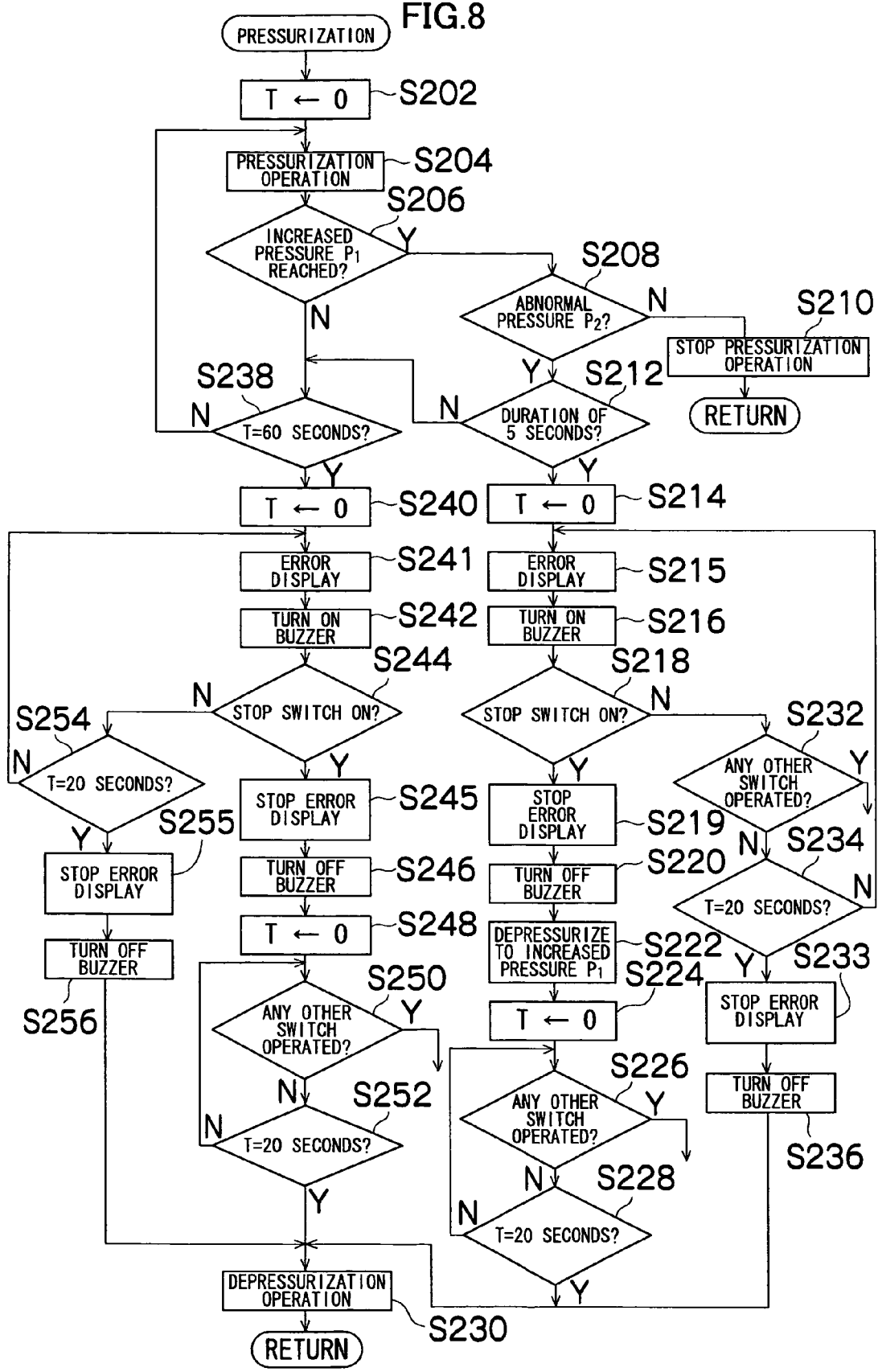
FIG. 8 is a flowchart showing the operation with respect to pressurization processing shown in FIG. 6.

Pressurization processing will be described with reference to the flowchart of FIG. 8.

The sequencer 170 first resets time T in the timer to 0 (step S202) and thereafter operates the control system A for pressurization (step S204). That is, the sequencer 170 turns on the electromagnetic valve VA3 and drives the pump PA1 for pressurization.

Subsequently, the sequencer 170 determines from the detection signal from the pressure sensor SA whether or not the pressure in the tube 110 has reached the increased pressure $P_1$ set in advance (step S206). If the pressure in the tube 110 has reached the increased pressure $P_1$, the sequencer 170 further determines whether or not the pressure in the tube 110 has reached the abnormal pressure $P_2$ (step S208). If the pressure in the tube 110 has not reached the abnormal pressure $P_2$, the sequencer 170 stops the pressurization operation (step S210). The pressurization operation is stopped by means of the electromagnetic valve VA1. Since the diameter of the air supply tube provided along the insertion portion 12 of the balloon-type endoscope 10 is sufficiently smaller than the diameter of the tube 110, the pressure in the tube 110 reaches the increased pressure $P_1$ before the pressure in the first balloon 60 reaches the increased pressure $P_1$ after the start of supply of air (pressurization). The pressurization operation is thereby stopped. However, if the pressure in the first balloon 60 has not reached the increased pressure $P_1$, the pressure in the tube 110 is again reduced to become lower than the increased pressure $P_1$. In this case, the sequencer 170 again starts the pressurization operation by referring to the detection signal from the pressure sensor SA1. Thus, starting the pressurization operation and stopping the pressurization operation are repeated a certain number of times to adjust the pressure in the first balloon 60 to the increased pressure $P_1$.

On the other hand, if the small intestine makes a vermicular movement, or if an abnormality in the main unit 120 (e.g., an abnormality of the electromagnetic valve VA1) causes failure to stop the pressurization operation, the pressure in the tube 110 may reach the abnormal pressure $P_2$. In such a case, the process moves from step S208 to step S212 and the sequencer 170 determines whether or not the abnormal pressure $P_2$ is maintained for five seconds.

If the abnormal pressure $P_2$ is maintained for five seconds, the sequencer 170 resets time T in the timer to 0, displays an error message and simultaneously sounds the buzzer BZ (steps S214, S215, and S216). As the error message, an error code (e.g., "Err4") and the balloon pressure value are alternately displayed on the pressure indicating portion 106.

The sequencer 170 thereafter determines whether the stop switch SW2 or SW5 is pressed (step S218). If the stop switch is pressed, the sequencer 170 stops displaying the error message and sounding the buzzer BZ (steps S219 and S220). The sequencer 170 then performs the depressurization operation until the reduction from the abnormal pressure $P_2$ to the increased pressure $P_1$ is completed (step S222). The depressurization operation is performed by turning off the electromagnetic valve VA3 for change to the depressurization side. In this case, even if failure to stop the pressurization operation occurs due to a malfunction of the electromagnetic valve VA1 for example, depressurization can be performed by changing the electromagnetic valve VA3.

Subsequently, the sequencer 170 resets time T in the timer to 0 (step S224) and determines whether or not an operation on any of the other switches SW, e.g., a switch SW6 turning off (depressurization) operation is performed (step S226). If none of the other switches SW is operated during 20 seconds (step S228), the process advances to step S230 and the sequencer 170 performs a depressurization operation for depressurization to the negative pressure $P_3$. If the sequencer 170 determines in step S226 that one of the other switches SW has been operated, it performs balloon control on the basis of the command from the switch SW.

If the sequencer 170 determines in step S218 that neither of the stop switch SW2 nor SW5 has been pressed, it then determines whether or not an operation on any of the other switches SW is performed (step S232). If a state in which neither of the stop switch SW2 nor SW5 is pressed and none of the other switches is operated continues for 20 seconds (step S234), the sequencer 170 stops displaying the error message and sounding the buzzer (steps S235 and S236) and performs a depressurization operation for depressurization to the reduced pressure $P_3$ (step S230).

On the other hand, if back in step S206 the pressure in the tube 110 does not reach the increased pressure $P_1$ during the pressurization operation, the sequencer 170 determines whether or not time T from the start of pressurization operation has reached 60 seconds (step S238). In the case of repeating the processing through step S204, S206, and S238 before time T reaches 60 seconds, the sequencer 170 determines that there is an abnormality (for example, the tube 110 and the balloon air supply port 18 are not connected).

If the sequencer 170 detects an abnormality as described above, it resets time T in the timer to 0, displays an error message and simultaneously sounds the buzzer BZ (steps S240, S242). As the error message, an error code (e.g., "Err5") and the value of pressure in the first balloon 60 are alternately displayed on the pressure indicating portion 106.

The sequencer 170 thereafter determines whether the stop switch SW2 or SW5 is pressed (step S244). If the stop switch is pressed, the sequencer 170 stops displaying the error message and sounding the buzzer BZ (step S246). Subsequently, the sequencer 170 resets time T in the timer to 0 (step S248) and determines whether or not any of the other switches is operated (step S250). If none of the other switches is operated during 20 seconds from stopping the buzzer BZ (step S252), the process advances to step S230 and the sequencer 170 performs a depressurization operation for reduction to the negative pressure $P_3$. If the sequencer 170 determines that one of the other switches SW has been operated, it performs balloon control on the basis of the command from the switch SW.

On the other hand, if in step S244 neither of the stop switch SW2 nor SW5 is pressed, the sequencer 170 determines whether or not a time period of 20 seconds has lapsed time T after starting sounding the buzzer BZ (step S254). If a time period of 20 seconds has lapsed, the sequencer 170 automatically stops displaying the error message and sounding the buzzer BZ (step S256). The process thereafter advances to step S230 and the sequencer 170 performs a depressurization operation for depressurization to the negative pressure $P_3$.

Abnormality detection in a case where the first balloon 60 is broken will next be described.

Since the diameter of the air supply tube provided along the insertion portion 12 of the balloon-type endoscope 10 is smaller than the diameter of the tube 110 (the diameter of the tube 110 is about 6 mm and the diameter of the air supply tube is about 0.8 mm), the pressure in the tube 110 reaches the increased pressure $P_1$ before the pressure in the first balloon 60 reaches the increased pressure $P_1$ after the start of supply of air (pressurization). Pressurization operation is thereby stopped. However, when the pressure in the first balloon 60 is lower than the increased pressure $P_1$, air in the tube 110 is supplied to the first balloon 60 via the air supply tube and therefore, the pressure in the tube 110 is again reduced to become lower than the increased pressure $P_1$. In this case, the sequencer 170 again starts pressurization operation by referring to the detection signal from the pressure sensor SA1.

If the first balloon 60 is not broken, the pressure in the first balloon 60 can be adjusted to the increased pressure $P_1$ by repeating starting pressurization operation and stopping pressurization operation a certain number of times as described above. If the first balloon 60 is broken, the pressure in the first balloon 60 cannot be adjusted to the increased pressure $P_1$ even if starting pressurization operation and stopping pressurization operation are repeated during a long time period.

In this embodiment, in a case where repetition of starting pressurization operation and stopping pressurization operation at a short period (i.e., electromagnetic valve VA1 on-off chattering) is continued for a time period (e.g., 40 seconds) sufficiently longer than a chattering period which occurs during pressurization of the normal first balloon 60 in the shrunken state, it is determined that the first balloon 60 is broken, an error message is displayed and the buzzer is sounded. As the error message, an error code (e.g., "Err5") and the balloon pressure value are alternately displayed on the pressure indicating portion 106.

Figure 9:
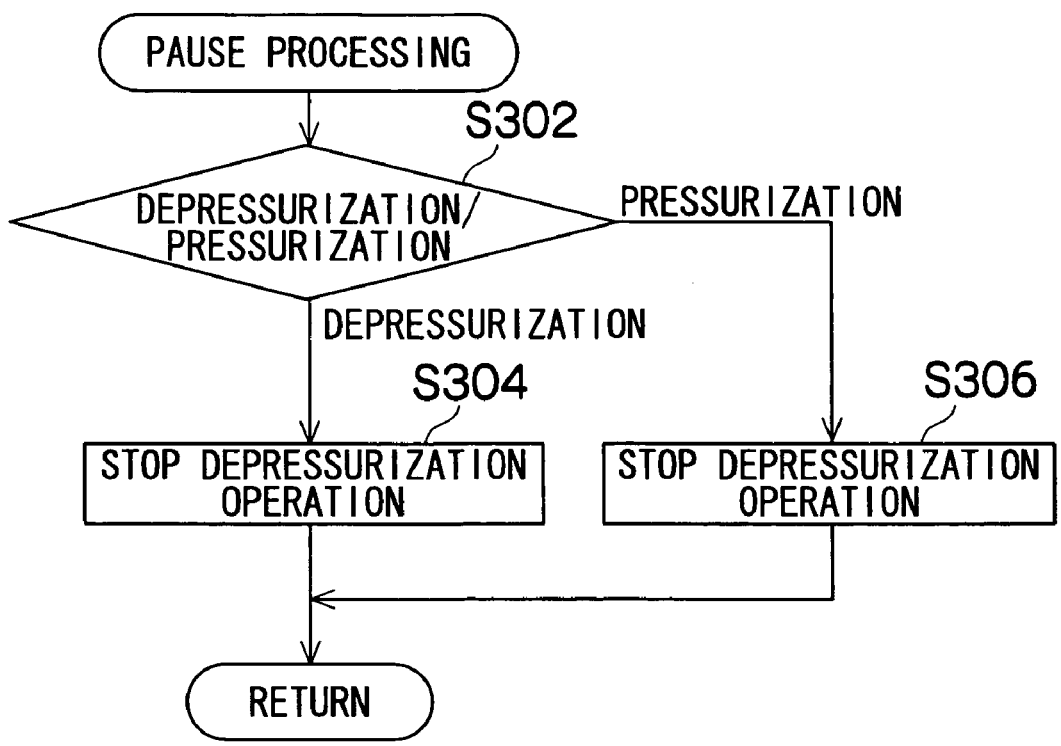
FIG. 9 is a flowchart showing the operation with respect to pause processing shown in FIG. 6.

Pause processing will be described with reference to the flowchart of FIG. 9.

The sequencer 170 determines whether a pause command to maintain the pressure in the first balloon 60 has been input (by turning on the pause switch SW7) during a depressurization operation or a pressurization operation (step S302). If the pause command has been input during a depressurization operation, the sequencer 170 changes the electromagnetic valve VA2 to stop the depressurization operation (step S304).

If the pause command has been input during a pressurization operation, the sequencer 170 changes the electromagnetic valve VA1 to stop the pressurization operation (step S306).

This pause function is used, for example, when the double-balloon-type endoscope is inserted while expanding the balloons in the large intestine. That is, in some case of pressurization of the balloons in the large intestine whose lumen is larger in diameter than that of the small intestine, the pressure in each balloon is not increased to the increased pressure $P_1$ set in advance even if the size of the balloon is not smaller than the size of the lumen. In such a case, the above-described pause function is used to stop the pressurization operation.

If the pause switch SW7 is pressed during a temporary halt of depressurization or pressurization operation, the depressurization or pressurization operation before the temporary halt is resumed. Further, if the pressurization or depressurization switch (endoscope on/off switch SW6) is pressed during a temporary halt of depressurization or pressurization operation, the operation corresponding to the pressed switch is performed with priority.

The pressure indicating portions 106 and 108 on which the values of pressures in the two balloons 60 and 80 are indicated will be described.

Figure 10:
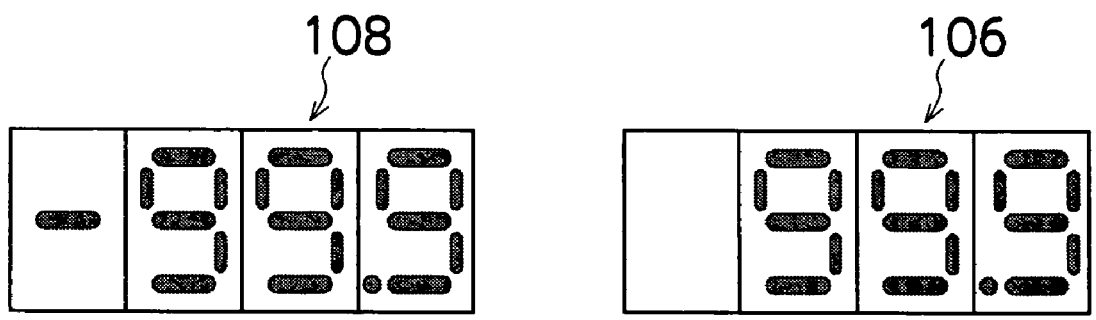
FIG. 10 is a diagram showing an example of display on pressure indicating portions shown in FIG. 3.

Each of the pressure indicating portions 106 and 108 is constructed by using a combination of four single-figure display units capable of displaying "0" to "9". As shown in FIG. 10, pressure values can be displayed by selecting from numeric values "–99.9" and "99.9" and other values between "–99.9" and "99.9". On the pressure indicating portions 106 and 108, pressure values are normally displayed in green. When an abnormality occurs, an error message is displayed by lighting in red. Eight error messages sorted in correspondence with kinds of abnormalities are displayed as error codes 1 to 8. The kind of abnormality and the method of displaying the abnormality with respect to each error code will be described below.

Figure 11:
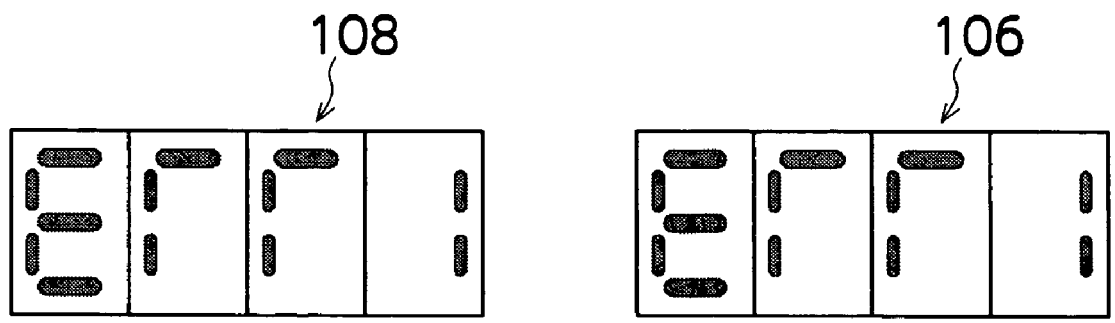
FIG. 11 is a diagram showing an example of display on the pressure indicating portions shown in FIG. 3.

In a case where an initial diagnosis abnormality occurs when initial diagnosis is performed when the system is powered on (for example, a system error such as a high residual potential occurs), "Err1" is displayed on the pressure indicating portions 106 and 108, as shown in FIG. 11. In a case where a system error such as freeze of a piece of software occurs during operation, "Err2" is displayed as F/W runaway on the pressure indicating portions 106 and 108. In a case where an error such as failure to perform depressurization processing occurs due to coming off of the tube or the like during an initial operating status transition, "Err3" is displayed as an initial depressurization error on the pressure indicating portions 106 and 108. These error displays are produced on both the pressure indicating portions 106 and 108 and the message is displayed by lighting in red until the stop switch SW2 or SW5 is operated. The buzzer may be sounded simultaneously with the display of one of these messages.

Figure 12A:
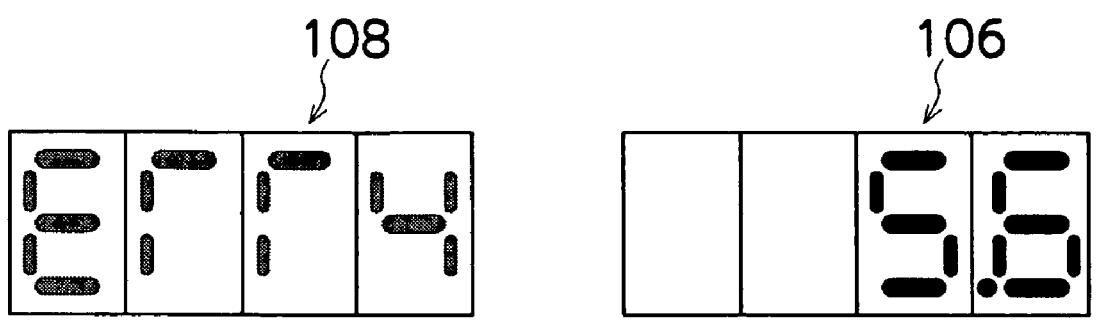
FIGS. 12A and 12B are diagrams showing an example of display on the pressure indicating portions shown in FIG. 3.
Figure 12B:
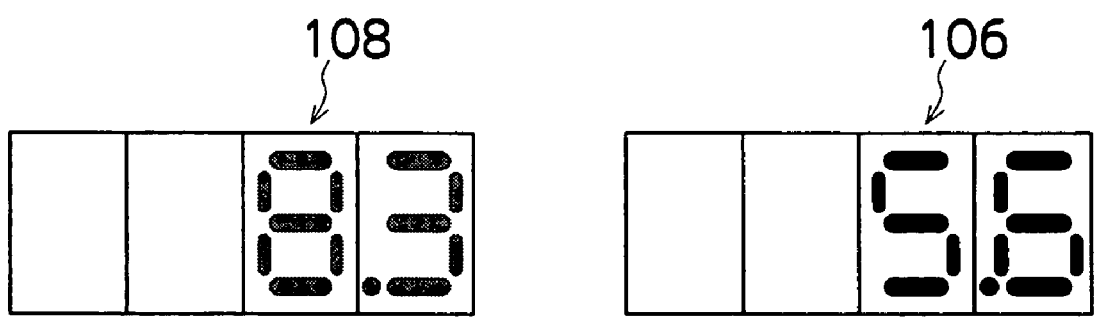

In a case where an abnormality occurs during depressurization processing or pressurization processing, one of "Err4" to "Err7" is displayed according to the details of the error as described above. This error display is produced on the pressure indicating portion 106 or 108 corresponding to the control system A or B in which the abnormality has occurred. That is, in a case where an abnormality occurs in the endoscope control system A on the first balloon 60 side, the error code is displayed on the pressure indicating portion 106. In a case where an abnormality occurs in the insertion assist implement control system B on the second balloon 80 side, the error code is displayed on the pressure indicating portion 108. Further, in these error code displays, the error code and the measured value from the pressure sensor SA or SB are alternately displayed. FIGS. 12A and 12B show an example of display in a case where an "abnormal pressure" occurs in the insertion assist implement control system B on the second balloon 80 side. In this case, the error code "Err4" is first displayed on the pressure indicating portion 108 (FIG. 12A), the display on the pressure indicating portion 108 is then changed to a pressure value "8.3" (FIG. 12B), and these display contents are alternately displayed. Display switching between the error code and the pressure value is performed at intervals of several seconds (e.g., 0.5 to 2 seconds). While this display is produced on the pressure indicating portion 108, a pressure value "5.6" is continuously displayed on the pressure value indicating portion 106. This display method enables the operator to identify the control system A or B as a place in which an abnormality has occurred as well as to grasp the occurrence of the abnormality. This display method also enables the operator to grasp the values of pressures in the balloons 60 and 80 when the abnormality exists.

Figure 13A:
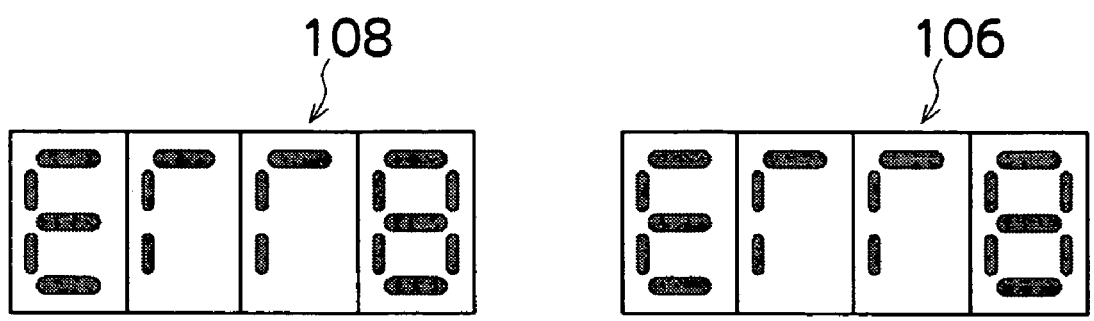
FIGS. 13A and 13B are diagrams showing an example of display on a balloon monitor.
Figure 13B:
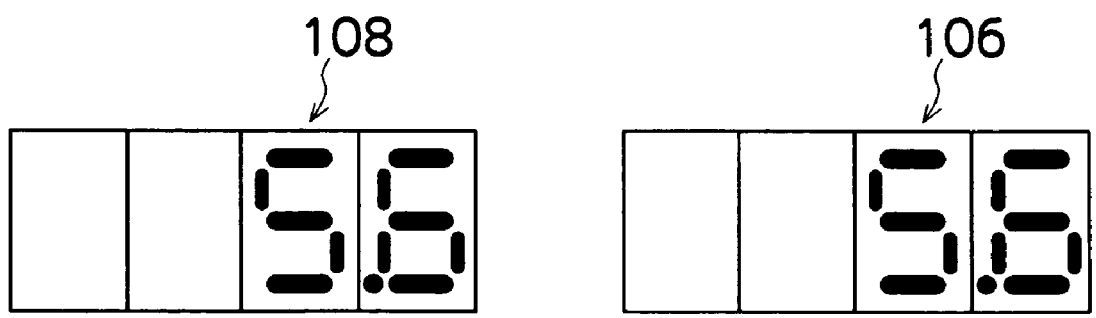

If a malfunction of the cooling fan 190 occurs in any of the processings described above, "Err8" is first displayed on the two pressure indicating portions 106 and 108, as shown in FIG. 13A. Pressure values (e.g., "5.6") such as shown in FIG. 13B and the error code shown in FIG. 13A are alternately displayed. Thus, each processing can be performed without being interrupted. Preferably, in this case, the time period during which the pressure values are displayed is longer than the time period during which the error code is displayed.

In this embodiment, as described above, an error message (error code) is displayed on the pressure indicating portions 106 and 108 when an abnormal condition occurs. The operator operates the endoscope apparatus while seeing the pressure indicating portions 106 and 108 and, therefore, can immediately recognize the occurrence of an abnormal condition if an error code is displayed on the pressure indicating portions 106 and 108. The operator can also grasp immediately what the abnormal condition is, since the error code is displayed by being selected from codes representing possible kinds of abnormal condition. When pressurization processing or depressurization processing is being performed, an error code and a pressure value are alternately displayed. Therefore, even when the apparatus is in an abnormal condition, the operator can know the values of the pressures in the balloons 60 and 80 and accurately grasp the abnormal condition.

In this embodiment, an error message is displayed on the pressure indicating portions 106 and 108. Therefore there is no need to provide a panel and a warning lamp for an error message and the size and the cost of the controller can be reduced. In particular, in this embodiment, an error message is displayed as a code and, therefore, a panel of a simple structure on which a numeric figure is displayed may be selected as the pressure indicating portions 106 and 108, thus enabling the controller to be further reduced in size and cost.

In the above-described embodiment, an error code representing the kind of an abnormal condition is displayed on the pressure indicating portions 106 and 108 at the time of occurrence of the abnormal condition. However, the present invention is not limited to this. Different colors respectively associated with kinds of the abnormal condition may be used for indication of abnormalities. In such a case, pressure values are displayed on the pressure indicating portions 106 and 108 at all times and, therefore, the conditions of the balloons can be accurately grasped at all times.

What is claimed is:

1. A balloon controller for an endoscope apparatus which is connected to a balloon attached to an insertion portion of an endoscope or to a balloon attached to an insertion assist implement for guiding the insertion portion when the insertion portion is inserted, and which controls expansion and shrinkage of the balloon by supplying a fluid to the balloon or drawing the fluid from the balloon, the balloon controller comprising:

a pressure indicating portion on which the value of pressure in the balloon is displayed; and an abnormal pressure condition determining portion that determines an abnormal pressure condition to be present in the endoscope apparatus, wherein an error message indicating the abnormal pressure condition in the endoscope apparatus determined by the abnormal pressure condition determining portion is displayed on the pressure indicating portion, and wherein the display of the error message and the display of the value of pressure in the balloon are alternately displayed on the same display area of the pressure indicating portion by being switched in a certain period of time.

2. The balloon controller for the endoscope apparatus according to claim 1, wherein the error message is displayed as an error code having a numeric figure indicating the kind of the abnormal pressure condition.

3. The balloon controller for the endoscope apparatus according to claim 2, wherein the pressure indicating portion is provided on a main body of the balloon controller.

4. The balloon controller for the endoscope apparatus according to claim 1, wherein the pressure indicating portion is provided on a main body of the balloon controller.

5. The balloon controller for the endoscope apparatus according to claim 1, wherein the abnormal pressure condition determining portion includes a timer.

6. A balloon controller for an endoscope apparatus which is connected to a balloon attached to an insertion portion of an endoscope and to a balloon attached to an insertion assist implement for guiding the insertion portion when the insertion portion is inserted, and which controls expansion and shrinkage of each balloon by supplying a fluid to the balloon or drawing the fluid from the balloon, the balloon controller comprising:

a pressure indicating portion on which the value of pressure in the balloon on the insertion portion of the endoscope is displayed;

an another pressure indicating portion on which the value of pressure in the balloon on the insertion assist implement is displayed; and an abnormal pressure condition determining portion that determines an abnormal pressure condition to be present in either one of the two balloons of the endoscope apparatus, wherein when an abnormal pressure condition of either one of the two balloons is determined to have occurred by the abnormal pressure condition determining portion, an error message is displayed on the pressure indicating portion corresponding to the balloon having been determined by the abnormal pressure condition determining portion to have the abnormal pressure condition, and wherein the display of the error message and the display of the value of pressure in the balloon are alternately displayed on the same display area of the pressure indicating portion by being switched in a certain period of time.

7. The balloon controller for the endoscope apparatus according to claim 6, wherein the error message is displayed as an error code having a numeric figure indicating the kind of the abnormal pressure condition.

8. The balloon controller for the endoscope apparatus according to claim 7, wherein the pressure indicating portion is provided on a main body of the balloon controller.

9. The balloon controller for the endoscope apparatus according to claim 6, wherein the pressure indicating portion is provided on a main body of the balloon controller.

10. The balloon controller for the endoscope apparatus according to claim 6, wherein the abnormal pressure condition determining portion includes a timer.

* * * * *